(12) United States Patent
Deffieux et al.

(10) Patent No.: US 10,952,701 B2
(45) Date of Patent: Mar. 23, 2021

(54) DETECTING APPARATUS AND ASSOCIATED IMAGING METHOD

(71) Applicants: INSTITUT NATIONAL DE LA SANTE ET DE LA RECHERCHE MEDICALE (INSERM), Paris (FR); UNIVERSITÉ PIERRE ET MARIE CURIE (PARIS 6), Paris (FR); UNIVERSITÉ PARIS DIDEROT—PARIS 7, Paris (FR); CENTRE NATIONAL DE LA RECHERCHE SCIENTIFIQUE, Paris (FR); ECOLE SUPERIEURE DE PHYSIQUE ET DE CHIMIE INDUSTRIELLES DE LA VILLE DE PARIS, Paris (FR)

(72) Inventors: Thomas Deffieux, Paris (FR); Jean-Luc Gennisson, Paris (FR); Mickaël Tanter, Paris (FR); Ivan Cohen, Paris (FR); Mathieu Pernot, Paris (FR)

(73) Assignees: INSTITUT NATIONAL DE LA SANTE ET DE RECHERCHE MEDICAL (INSERM), Paris (FR); UNIVERSITE PIERRE ET MARIE CURIE (PARIS 6), Paris (FR); UNIVERSITE PARIS DIDEROT—PARIS 7, Paris (FR); CENTRE NATIONAL DE LA RECHERCHE SCIENTIFIQUE, Paris (FR); ECOLE SUPERIEURE DE PHYSIQUE ET DE CHIMIE INDUSTRIELLES DE LA VILLE DE PARIS, Paris (FR)

( * ) Notice: Subject to any disclaimer, the term of this patent is extended or adjusted under 35 U.S.C. 154(b) by 556 days.

(21) Appl. No.: 15/735,759
(22) PCT Filed: Jun. 16, 2016
(86) PCT No.: PCT/EP2016/063954
§ 371 (c)(1),
(2) Date: Dec. 12, 2017

(87) PCT Pub. No.: WO2016/202955
PCT Pub. Date: Dec. 22, 2016

(65) Prior Publication Data
US 2018/0177487 A1    Jun. 28, 2018

(30) Foreign Application Priority Data

Jun. 16, 2015    (EP) .................................. 15305937

(51) Int. Cl.
*A61B 8/00* (2006.01)
*A61B 8/08* (2006.01)
(Continued)

(52) U.S. Cl.
CPC .......... *A61B 8/4209* (2013.01); *A61B 8/0808* (2013.01); *A61B 8/0816* (2013.01);
(Continued)

(58) Field of Classification Search
CPC ... A61B 8/4209; A61B 8/0808; A61B 8/0816; A61B 8/145; A61B 8/4411;
(Continued)

(56) References Cited

U.S. PATENT DOCUMENTS

| 2011/0112405 A1 | 5/2011 | Barthe et al. |
| 2011/0251489 A1 | 10/2011 | Zhang et al. |

FOREIGN PATENT DOCUMENTS

| DE | 41 31 420 A1 | 3/1993 |
| DE | 94 05 271 U1 | 8/1994 |

(Continued)

*Primary Examiner* — Bo Joseph Peng
(74) *Attorney, Agent, or Firm* — W&C IP

(57) ABSTRACT

The invention concerns a detecting apparatus (12) for imaging at least two areas of a brain of a subject (10), the detecting apparatus (12) comprising: —a holder comprising: —a frame (14) devoted to be cemented on the skull of the subject (10), the frame (14) delimitating an inner portion
(Continued)

(18) which is transparent to ultrasound waves, —a removable imaging device comprising: —a platform (16) delimitating an inner space (28), the inner space (28) facing the inner portion (18), —a fixing element (30) adapted to temporary fix and lock the platform (16) to the holder, —an ultrasound probe (32), and —a moving stage (34) holding the ultrasound probe (32) and being adapted to move the ultrasound probe (32) within the inner space (28).

14 Claims, 9 Drawing Sheets

(51) Int. Cl.
    *A61B 8/14*     (2006.01)
    *A61B 5/00*     (2006.01)
    *A61B 5/0478*     (2006.01)

(52) U.S. Cl.
    CPC ............ *A61B 8/145* (2013.01); *A61B 8/4411* (2013.01); *A61B 8/4416* (2013.01); *A61B 8/4461* (2013.01); *A61B 8/4488* (2013.01); *A61B 8/543* (2013.01); *A61B 5/0077* (2013.01); *A61B 5/0478* (2013.01); *A61B 8/488* (2013.01); *A61B 2503/40* (2013.01); *A61B 2562/0219* (2013.01)

(58) Field of Classification Search
    CPC ..... A61B 8/4416; A61B 8/4488; A61B 8/543; A61B 8/4461; A61B 8/488; A61B 5/0077; A61B 5/0478; A61B 2503/40; A61B 2562/0219
    See application file for complete search history.

(56) References Cited

FOREIGN PATENT DOCUMENTS

| | | |
|---|---|---|
| EP | 0 409 822 A1 | 1/1991 |
| WO | 2007/044469 A2 | 4/2007 |

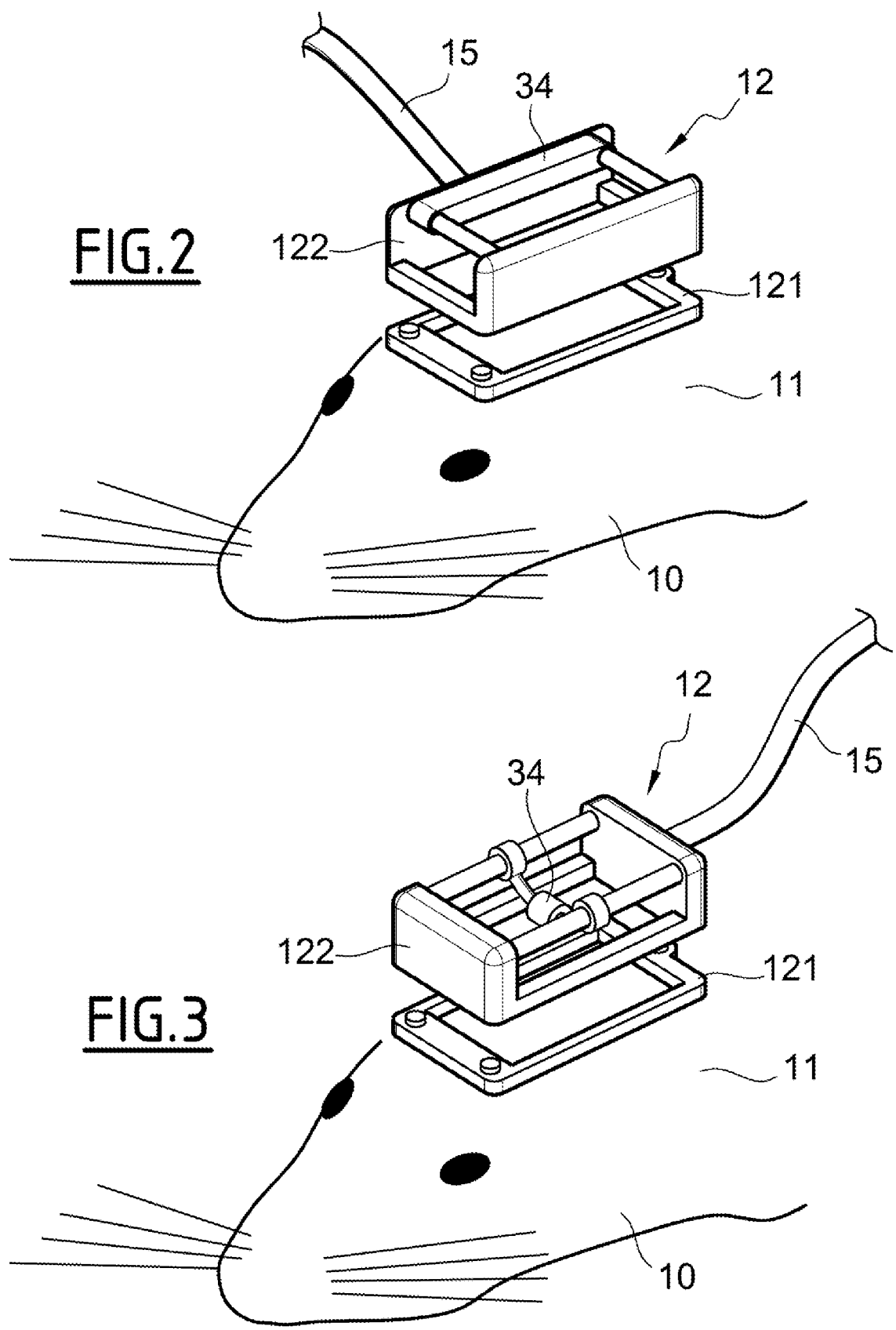

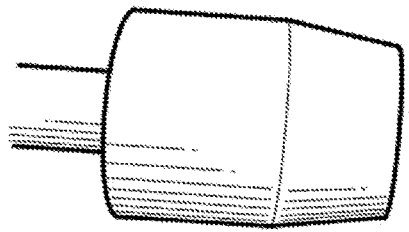
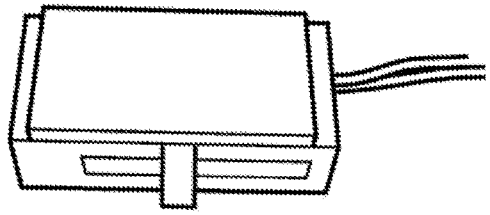
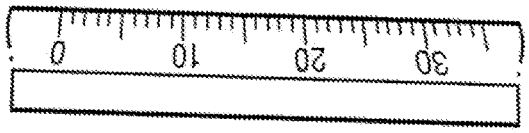
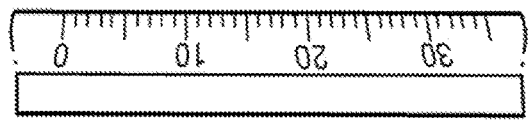
FIG.25　　　　　　　　　　FIG.26
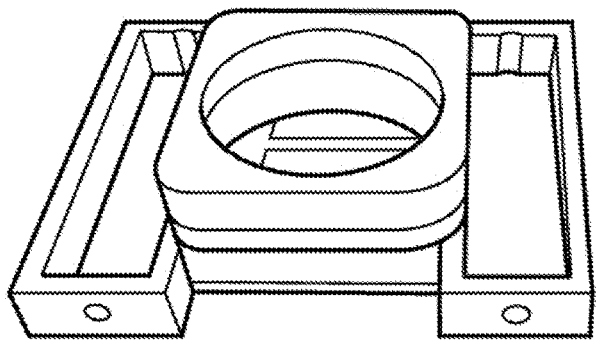
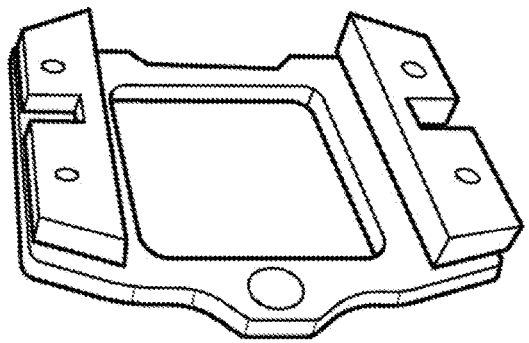
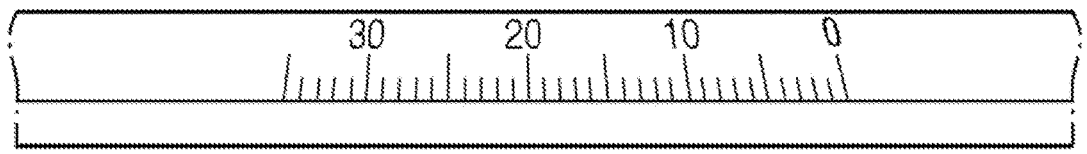
FIG.27

DETECTING APPARATUS AND ASSOCIATED IMAGING METHOD

TECHNICAL FIELD OF THE INVENTION

The present invention concerns a detecting apparatus and a method for imaging at least two areas of a brain of a subject using such detecting apparatus.

BACKGROUND OF THE INVENTION

In vivo brain activity recordings provide a unique contribution to neuroscience to unravel the underlying mechanisms of complex behaviors and pathologies. Ideally, it is desired to capture instantly both neuronal processing and metabolic events, which form two major facets of global brain equilibrium, in the most natural conditions, that is when the subject is awake and freely moving.

Practice is a compromise between the size of imaging field, time resolution, sensitivity, separability of processing and metabolism, and physical constraint on the animal. Electrophysiology and more recently optical techniques can record neuronal activity in the mobile animal, yet sampling is limited, respectively, by electrode size and light diffraction.

Conversely, functional magnetic resonance imaging records brain-wide metabolic adaptation, with tradeoffs in sensitivity and resolution, at the cost of subject immobilization or animal sedation.

Functional ultrasound imaging based on ultrafast Doppler offers a way to monitor brain hemodynamics and functional connectivity in rodents with high spatiotemporal resolution and unique sensitivity.

It is known several medical systems to interact with a skull, and notably applying ultrasound waves.

Document DE 41 31 430 A1 discloses that a probe holder including a handpiece for the probe, which compared to the holding plate, is located so that it can be swiveled as required in the probe holder. The probe holder also has a guide piece with a lateral attachment. The attachment has at least one flat edge, for engaging in an open slot at the holding plate. The guide piece has an external thread, for the screwing on of a retaining nut. The dial of the nut is larger than the width of the opening of the holding plate. The guide piece has a spherical cover with an opening. Such probe holder is used in medical ultrasonic diagnosis. This probe holder is designed so that it can be matched to individual patient, provides wide range of adjustment, easy and exact adjustment also reliable over long periods. Parts made of plastic can be cost effectively produced.

Document US 2011/251489 A1 describes an ultrasound monitoring systems and components used in ultrasound monitoring systems, such as Transcranial Dopper (TCD) systems. Components include framework systems for mounting, locating and maintaining one or more ultrasound probes in contact with an anatomical surface, adjustable probe mounting systems, and probe interface components providing an acoustically transmissive interface between a probe mounting system and the emissive face of the ultrasound probe.

Document DE 94 05 271 U1 concerns an ultrasound probe.

Document WO 2007/044469 A1 relates to system and method for delivering radiation therapy to a target inside the head of a patient. A first reference coordinate system is defined in relation to anatomical landmarks on the patient's head which are visible externally and in images of the patient. The coordinates of a target are translated from the first reference coordinate system to a second reference coordinate system. The second reference coordinate system is defined in relation to an external locator device that is attached to the patient's head. The system comprises a treatment cap, locator device, sensor, ultrasound transducer, holder, and a variety of computer readable media. Angles are calculated to direct radiation to the target from the external locations selected with the locator device. Further, a treatment cap is produced that fits around the patient's head and holds interface units at certain positions and orientations. Each interface unit includes a movable transducer holder that holds a radiation source, and by rotating the transducer holders by the calculated angles, radiation is delivered to the target.

Document US 2011/112405 A1 discloses a dermatological cosmetic treatment and imaging system and method. In some embodiments, the system includes a hand wand with at least one finger activated controller, and a removable transducer module having an ultrasound transducer. In some embodiments, the system can include a control module that is coupled to the hand wand and has a graphical user interface for controlling the removable transducer module, and an interface coupling the hand wand to the control module. The interface may provide power to the hand wand or may transfer a signal from the hand wand to the control module. In some embodiments, the cosmetic treatment system may be used in cosmetic procedures on at least a portion of a face, head, neck, and/or other part of a patient.

Document EP 0 409 822 A1 proposes a neurosurgical auxiliary apparatus or a brain surgery adapter for neurosurgical procedures carried out through a craniotomy opening, such as imaging and/or tumor resection. The brain surgery adapter comprises an adapter frame (arranged to be clamped and sealed to the edges of the craniotomy opening; a preferably turnable imaging plate which comprises a slide space and which is arranged to be fitted in the frame and locked in position; and an ultrasonic transducer which is fitted in a transducer socket provided in the slide space of the imaging plate. When the adapter according to the invention is used, the ultrasonic transducer need not be supported manually. The adapter defines a closed liquid space, and it can also be provided with instruments for performing a neurosurgical operation, such as tumor resection. Imaging are carried out by means of the brain surgery adapter according to the invention in a determined imaging plane and the obtained images are accurately determined and comparable with each other irrespective of the fact that the tissue adapts itself during the tumor resection.

However, in all the previous mentioned systems, it is not possible to guaranty that the probe can be moved back and forth from one position to another in stereotactic coordinates and without manual intervention on a moving subject.

SUMMARY OF THE INVENTION

The invention aims at enabling to deploy the potentialities of functional ultrasound imaging of the brain to awake and mobile animals.

To this end, the present specification describes a detecting apparatus for imaging at least two areas of a brain of a subject, the detecting apparatus comprising:
  a holder comprising:
    a frame devoted to be fixed, notably cemented, on a part of the skull of the subject, the frame delimitating an inner portion which is transparent to ultrasound waves, a removable imaging device comprising:
- a platform delimitating an inner space, the inner space facing the inner portion,
- a fixing element adapted to temporary fix and lock the platform to the holder,
- an ultrasound probe comprising one or more transducer arrays, and
- a moving stage holding the ultrasound probe and being adapted to move the ultrasound probe within the inner space.

Thanks to the detecting apparatus, it becomes possible to image several locations on the same awake and mobile subject in a very easy way.

The proposed detecting apparatus allows for direct positioning of the ultrasound probe over a specific brain structure in stereotactic coordinates, move and possibly come back to the exact same plane without any manual intervention and all while the subject is awake and moving. The proposed detecting apparatus enables to image different brain structures with precision in an awake animal during a unique recording session.

According to further aspects of the invention which are advantageous but not compulsory, the detecting apparatus might incorporate one or several of the following features, taken in any technically admissible combination:
- a first area of the brain is distinct from a second area of the brain.
- the moving stage is adapted to move between a first position wherein the first area of the brain is imaged with the ultrasound probe and a second position wherein the second area of the brain is imaged with the ultrasound probe.
- the holder further comprises a window transparent to ultrasound waves, the window being inserted in the frame such that the window corresponds to the inner portion.
- the fixing element and the frame are magnetic.
- the frame further comprises an element having a first shape, the fixing element having a second shape, the first shape and the second shape being complementary.
- each transducer array is a linear transducer array.
- the moving stage comprises a movable screw.
- the moving stage further comprises a motor adapted to move the screw and a controller adapted to command the motor with a command law.
- the command law depends on at least one of the following elements:
  - the amplitude of reflected ultrasound signal obtained by the ultrasound probe over an object with a known position such as a wire or bead,
  - images obtained by the ultrasound probe using a Doppler technique,
  - images obtained by the ultrasound probe using an ultrasensitive Doppler technique, and
  - a reference structural atlas.
- the removable imaging device further comprises at least one additional sensor adapted to provide a continuous signal, each additional sensor being chosen among an electrode, a surface electrode array, an implanted electrode, an electrode array, an accelerometer, a camera adapted to film the subject and the command law depends from the signal from the additional sensor.
- the command law depends on a combination of the conditions previously defined.
- the removable imaging device further comprises a unique cable and the controller is further adapted to process data issued from the ultrasound probe, the cable being positioned between the platform and the controller.
- the moving stage is a translating stage adapted to translate the ultrasound probe within the inner space.
- the moving stage is a rotating stage adapted to rotate the ultrasound probe around an axis within the inner space.

The specification also relates to a method for imaging at least two areas of a brain of a subject, the method comprising the steps of:
- providing a holder comprising:
  - a frame devoted to be fixed, notably cemented, on a part of the skull of the subject, the frame delimitating an inner portion which is transparent to ultrasound waves,
- fixing, notably cementing, the frame to the part of the skull of the subject,
- providing a removable imaging device comprising:
  - a platform delimitating an inner space, the inner space facing the inner portion,
  - a fixing element adapted to temporary fix and lock the platform to the holder,
  - an ultrasound probe comprising one or more transducer arrays, and
  - a moving stage holding the ultrasound probe and being adapted to move the ultrasound probe within the inner space,
- fixing the platform to the holder with the fixing element,
- imaging a first area of the brain with the ultrasound probe,
- translating the ultrasound probe with the moving stage, and
- imaging a second area of the brain with the ultrasound probe.

According to a preferred embodiment, the subject is awake.

BRIEF DESCRIPTION OF THE DRAWINGS

The invention will be better understood on the basis of the following description which is given in correspondence with the annexed figures and as an illustrative example, without restricting the object of the invention. In the annexed figures:

FIG. 2 shows a subject holding another example of detecting apparatus;

FIG. 3 shows a subject holding another example of detecting apparatus, and

FIGS. 4 to 27 illustrates the results of experiments carried out by using an example of detecting apparatus.

DETAILED DESCRIPTION OF SOME EMBODIMENTS

Figure 1:
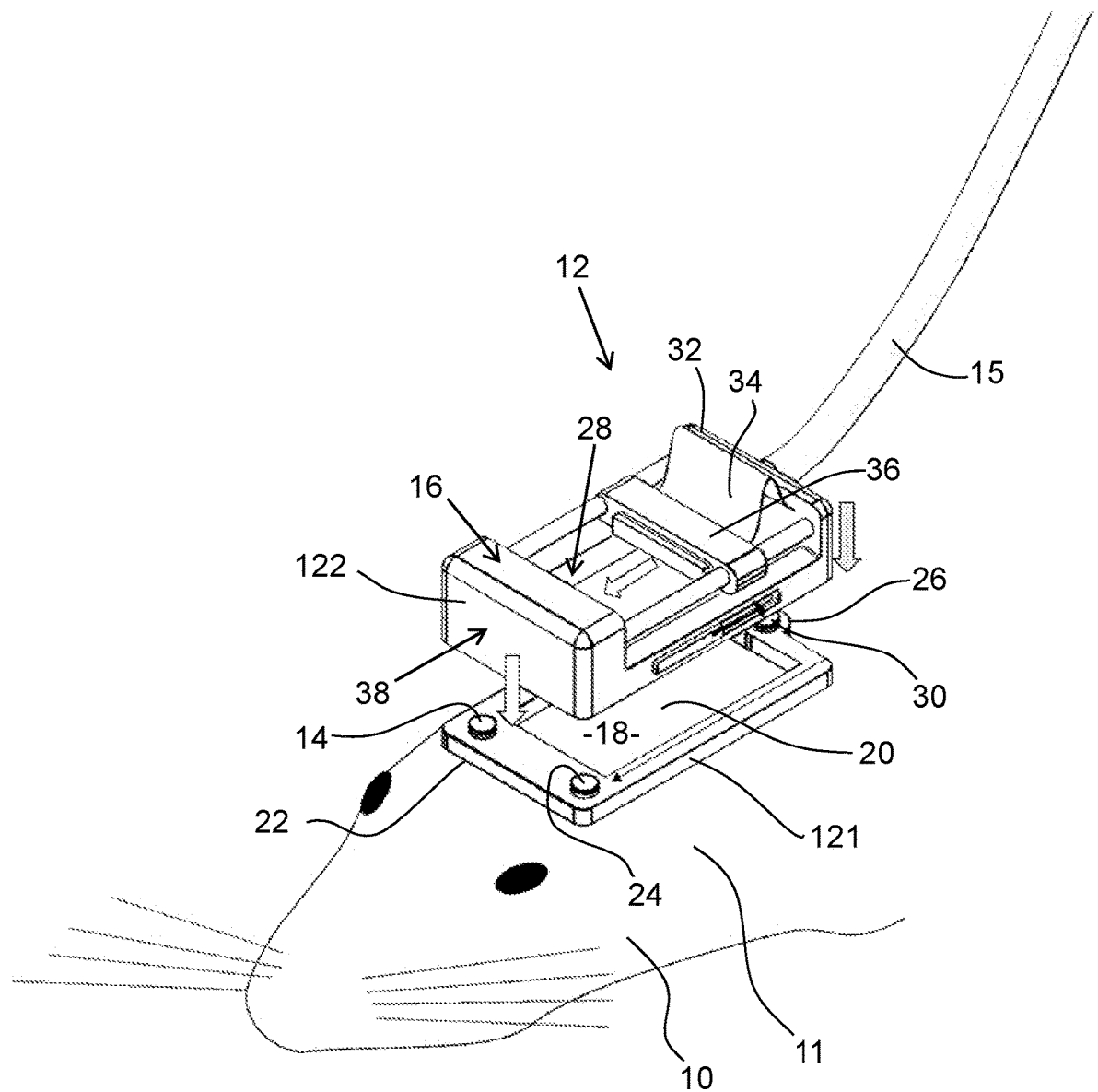
FIG. 1 shows a subject holding an example of detecting apparatus.
Figure 4:
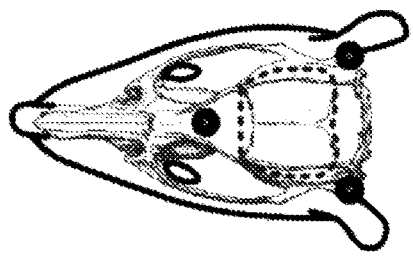
Figure 5:
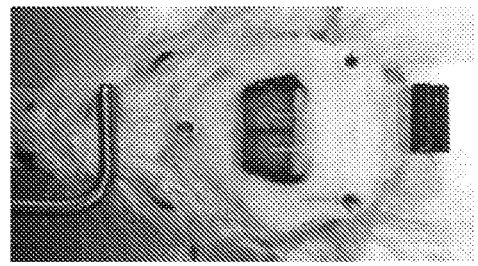
Figure 6:
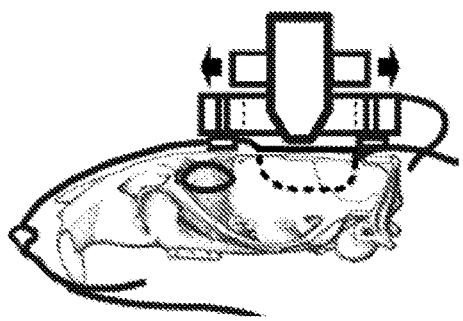
Figure 7:
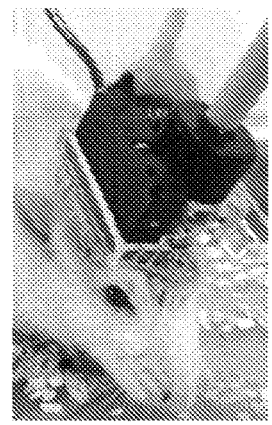
Figure 8:
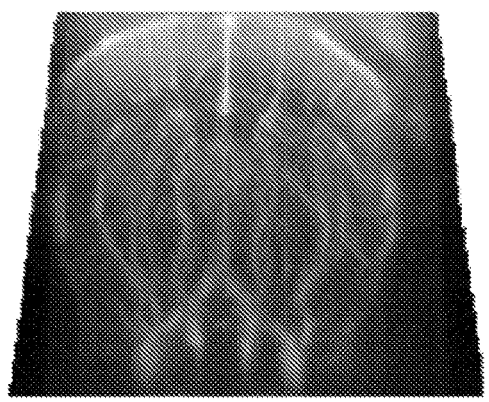

A subject 10 and a detecting apparatus 12 are illustrated on FIG. 1.

The subject 10 is a mouse.

More generally, the subject 10 is an animal for which at least one specific area is to be analyzed.

The specific area to be analyzed depends, for instance, of the kind of biological problem that is to be studied.

As an illustration, when the biological problem is memory, the area is a specific area of the hippocampus.

For the remainder of the specification, for illustrative purpose only, it is considered that the mouse suffers from epilepsy and that the areas to be analyzed are areas of the brain. In addition, it is considered that a first area of the brain and a second area of the brain different from the first area are to be imaged.

For this, the subject 10 has a head 11, the detecting apparatus 12 being maintained on the head 11 of the subject 10.

The detecting apparatus 12 is an apparatus adapted to detect at least one physical value in the areas of the brain of the subject 10.

The detecting apparatus 12 comprises a holder 121 and a removable imaging device 122.

The holder 121 comprises a frame 14, a window 20 and three elements 22, 24 and 26.

The frame 14 is devoted to be cemented on the skull of the subject 10.

The frame 14, illustrated on FIG. 1, has a polygonal shape.

The shape is rectangular in this specific case.

For an animal considered as small, such as a rat or a mouse, the length of the frame 14 is equal to the length of the brain of the animal. For instance, the length is 1 centimeter when the subject 10 is a mouse or the length is 2 centimeters when the subject 10 is a rat.

For an animal considered as big, such as a human, the length of the frame 14 is equal to a portion of the length of the brain of the animal. For instance, the length of the frame is inferior to 10 centimeters. More generally, the length of the frame 14 is equal to the minimum of the length of the brain of the animal and 10 centimeters.

The frame 14 is made in plexiglass.

The frame 14 delimitates an inner portion 18.

The inner portion 18 is made of polymethylpentene (TPX) and is almost transparent to ultrasound waves.

According to the example of FIG. 1, the inner portion 18 has a rectangular shape.

The window 20 is transparent to ultrasound waves.

The window 20 is inserted in the frame 14 such that the window 20 corresponds to the inner portion 18.

In the present case, the frame 14 has recesses in which part of the window 20 is inserted to ensure the holding of the window 20.

The window 20 is made in polymethylpentene.

The three elements 22, 24 and 26 have a first shape.

In the example of FIG. 1, each three elements 22, 24 and 26 has the same first shape.

The first shape of each three elements 22, 24 and 26 is cylindrical with a circular basis.

The removable imaging device 122 comprises a cable 15, a platform 16 delimitating an inner space 28, a fixing element 30, an ultrasound probe 32 and a moving stage 34.

The cable 15 is adapted to carry data from the ultrasound probe 32 to a controller.

In the specific example of FIG. 1, the cable 15 is a flexible cable. A flexible cable should be considered as a cable which enables to obtain a turn with diameter strictly inferior to 25 mm.

The inner space 28 is facing the inner portion 18.

The fixing element 30 is adapted to fix the platform 16 to the holder 121 in a removable way. In other words, the fixing element 30 is adapted to temporary fix and lock the platform 16 to the holder 121.

The fixing element 30 has a second shape, the first shape and the second shape being complementary.

The fact that the first shape and the second shape being complementary enables that the fixing element 30 and the three elements 22, 24 and 26 cooperate so as to ensure the removable fixing of the platform 16 to the holder 121.

In an alternative embodiment, the fixing element 30 and the frame 14 are magnetic.

According to the specific example of FIG. 1, the ultrasound probe 12 comprises a linear array of transducers.

The moving stage 34 holds the ultrasound probe 12.

In the case of FIG. 1, the moving stage 34 is a translating stage.

The translating stage is adapted to translate the ultrasound probe 12 within the inner space 28.

More precisely, the translating stage is adapted to translate the ultrasound probe 12 along the direction of the length of the frame 14.

According to the specific example of FIG. 1, the moving stage 34 is adapted to move between a first position wherein the first area of the brain is imaged with the ultrasound probe 32 and a second position wherein the second area of the brain is imaged with the ultrasound probe 32.

The translating stage 34 comprises a movable screw 36, a motor 38 and a controller not illustrated on FIG. 1.

The motor 38 is adapted to move the screw 36.

For instance, the motor 38 is a servomotor.

Alternatively, the motor 38 is step-by-step motor.

The controller is adapted to command the motor 38 with a command law.

In a specific embodiment, the command law depends from the detecting of ultrasound waves.

For instance, the command law depends from the magnitude of the reflected ultrasound waves detected.

In a more general way, the command law depends on at least one of the following elements:
  the amplitude of reflected ultrasound signal obtained by the ultrasound probe 32 over an object with a known position such as a wire or bead,
  images obtained by the ultrasound probe 32 using a Doppler technique,
  images obtained by the ultrasound probe 32 using an ultrasensitive Doppler technique, i.e. using more than 250 ultrasonic frames per second to estimate one Doppler image, and
  a reference structural atlas.

Alternatively, the removable imaging device 122 further comprises an electrode.

For instance, the electrode is an implanted electrode.

In such case, the command law depends from the detecting of ultrasound waves by the electrode.

More generally, the removable imaging device further comprises at least one additional sensor adapted to provide a continuous signal, each additional sensor being chosen among an electrode, an implanted electrode, an accelerometer, a camera adapted to film the subject 10 and the command law depends from the signal from the additional sensor.

According to an embodiment, the command law depends on a combination of the conditions previously defined.

Preferably, the command law depends on a combination of the conditions previously defined.

By the expression "conditional combination", it is meant that it is possible to take into account the information coming from an additional sensor to move the ultrasound probe 32 in a plane of specific interest. This enables to obtain a trade-off of two-dimensional imaging according to a specific protocol.

For instance, in the case the additional sensors are an electrode and a camera, if, on the one hand, the electrode provides a signal indicating a movement and that, on the other hand, the camera shows that the subject 10 does not move, the area linked to taking a decision in the brain of the subject 10 is of specific interest.

Alternatively, when both additional sensors show that the subject 10 is going to sleep, it can be interesting to image another area of the brain of the subject 10.

According to another example, if the camera shows that the subject 10 is interacting with an object, it can be desired to image the olfactory bulb or the sensorial cortex.

Operation of the detecting apparatus 12 is now described in reference to an example of carrying out of a method for imaging at least two areas of a brain of the subject 10.

The method for imaging comprises a step of providing the holder 121.

The method for imaging further comprises a step of cementing.

At the step of cementing, the frame 14 is cemented to a part of the skull of the subject 10.

As can be seen notably on FIGS. 4 to 7, intraparietal bones and frontal bones are parts of the skull of the subject 10 which can be used for cementing the frame 14.

The cementing step is carried out with dental cement.

The frame 14 constitutes an absolute frame for locating the detecting apparatus 12 with relation to the area of the brain to be imaged.

The method for imaging also comprises a step of providing the removable imaging device 122.

The method for imaging further comprises a step of fixing the platform 16 to the holder 121 by using the fixing element 30.

The method for imaging also comprises a step of imaging a first area of the brain with the ultrasound probe 32.

The method for imaging also comprises a step of translating the ultrasound probe 12 with the translating stage.

The translating enables the ultrasound probe 12 to pass from a first position to a second position. In the first position, the ultrasound probe 12 can image the first area whereas, in the second position, the ultrasound probe can image the second area.

The method for imaging also comprises a step of imaging a second area of the brain with the ultrasound probe 32.

Preferably, the second area is different from the first area.

Such method is very useful in so far as it can be used to image several locations on the same awake and mobile subject in a very easy way.

In other words, with the detecting apparatus proposed, it becomes possible to achieve three-dimensional imaging of a brain.

FIGS. 2 and 3 illustrate others examples of moving stage 34

In FIG. 2, the moving stage 34 is adapted to translate the ultrasound probe 12 in a direction perpendicular to the direction of the length of the frame 14.

In FIG. 3, the moving stage 34 is adapted to rotate the ultrasound probe 12 along an axis.

The embodiments and alternative embodiments considered here-above can be combined to generate further embodiments of the invention.

Experimental Section

Comments on the Figures

The experiments carried out are notably illustrated by FIGS. 4 to 27.

In a general way, FIGS. 4 to 13 illustrate awake/mobile EEG-f Ultrasound procedure and acquisition protocols.

FIGS. 4 to 8 illustrates the surgical procedure and probe setup. Notably, the window boundary is illustrated by a dotter line. It can also be seen the prosthetic skull, the attachment nuts, the probe holder, the motor and the probe. These figures also illustrate surgery outcome with added hippocampal stereotaxic electrode and EEG connector and the animal equipped with motorized translation stage and raw mfUS view through the prosthesis.

Figure 9:
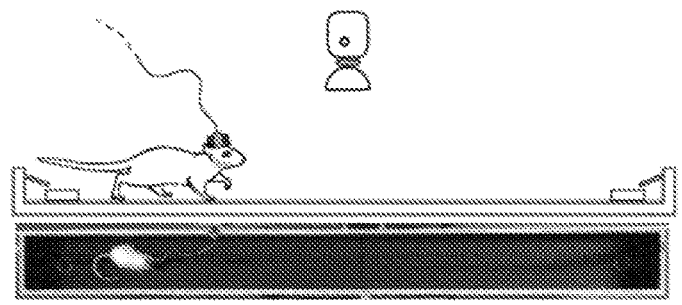
Figure 10:
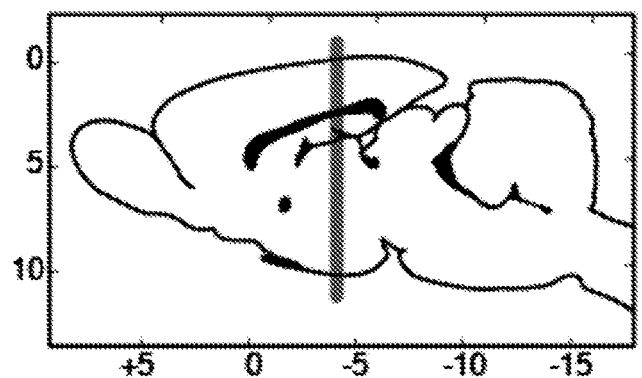
Figure 11:
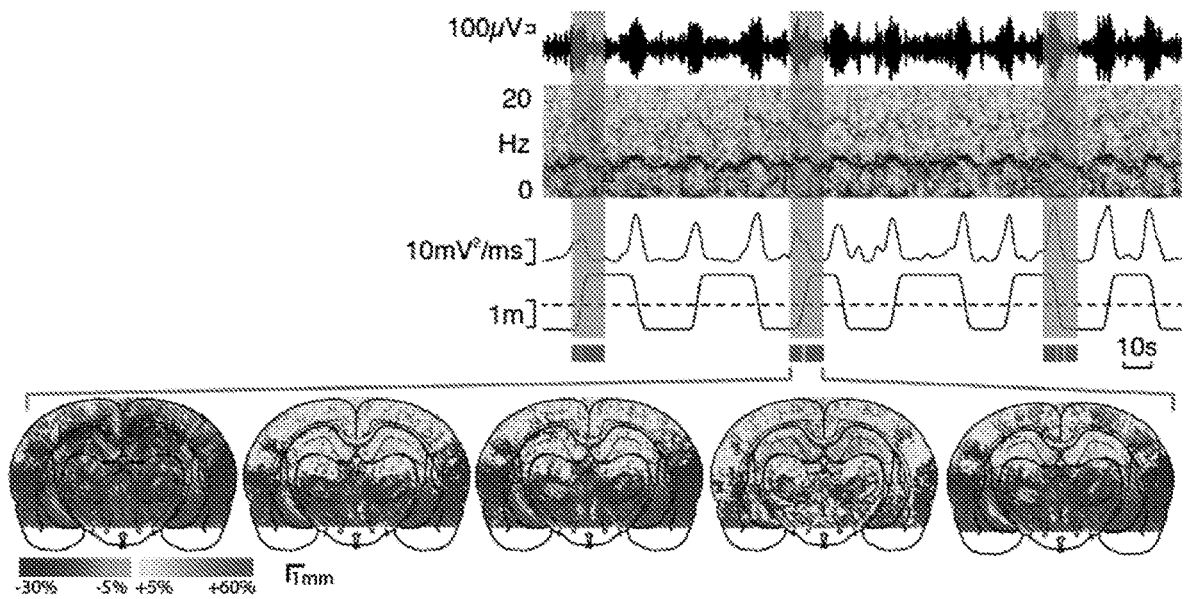

FIGS. 9 to 11 illustrate "burst mode" acquisition for maze experiments.

Schematic of the maze, water reward sites and overhead camera. Inset, atlas side view with the coronal imaging plane shown as red bar. Right: EEG-behavior recording chart from top to bottom, hippocampal local field potential (LFP), short term Fourier Transform time-frequency analysis showing a band at theta (6-9 Hz), and power in that band. The lower trace shows position along the maze, bottom red bars indicate timing of fUltrasound images. Hippocampal theta exhibits modulation during the task, peaking at top speed, corresponding to mid-maze crossing (dotted line), used as a time reference. Coronal ultrasound images acquired at high speed are averaged (n=25) for an example of 5 consecutive times around the reference. To increase burst duration the most ventral areas were not acquired.

Figure 12:
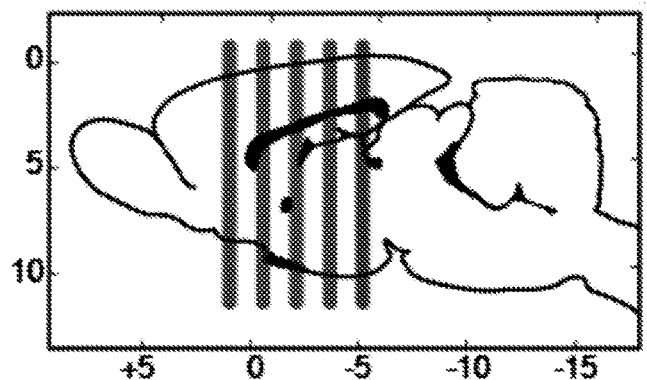
Figure 13:
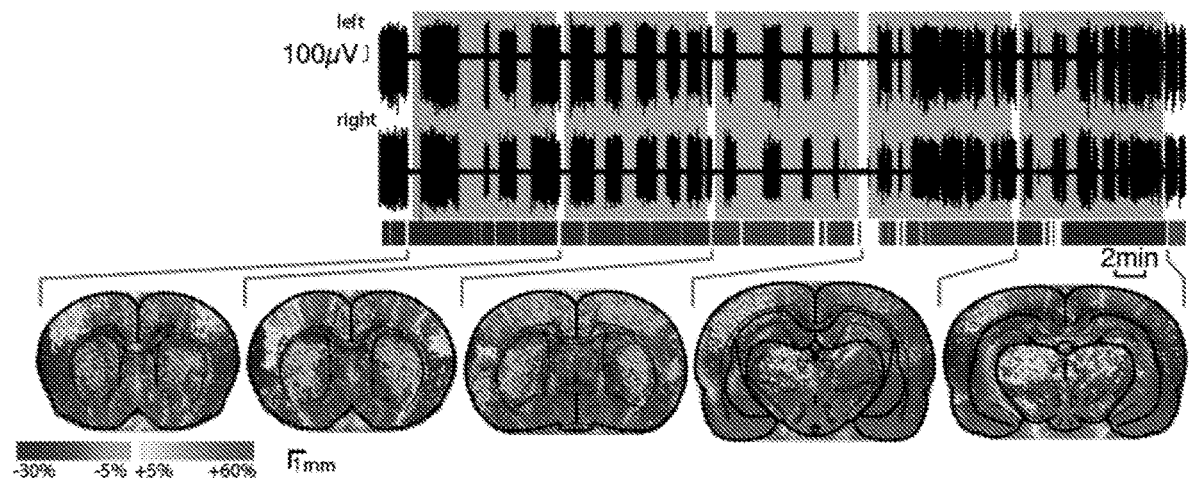

FIGS. 12 and 13 illustrate "continuous mode" acquisition for seizure recording.

Spontaneous generalized absence seizures are recorded from bilateral EEG. fUltrasound image trigger mark is shown below the EEG. Coronal planes indicated in the inset are acquired successively for 10 min each. Each color corresponds to a coronal plane.

For each FIGS. 9 to 13, changes in ultrasound image relative to baseline is shown where $p<10^{-2}$ with Bonferroni correction. Overlay from Paxinos atlas.

In a general way, FIGS. 14 to 20 illustrate a capture of natural events' hemodynamics.

Figure 14:
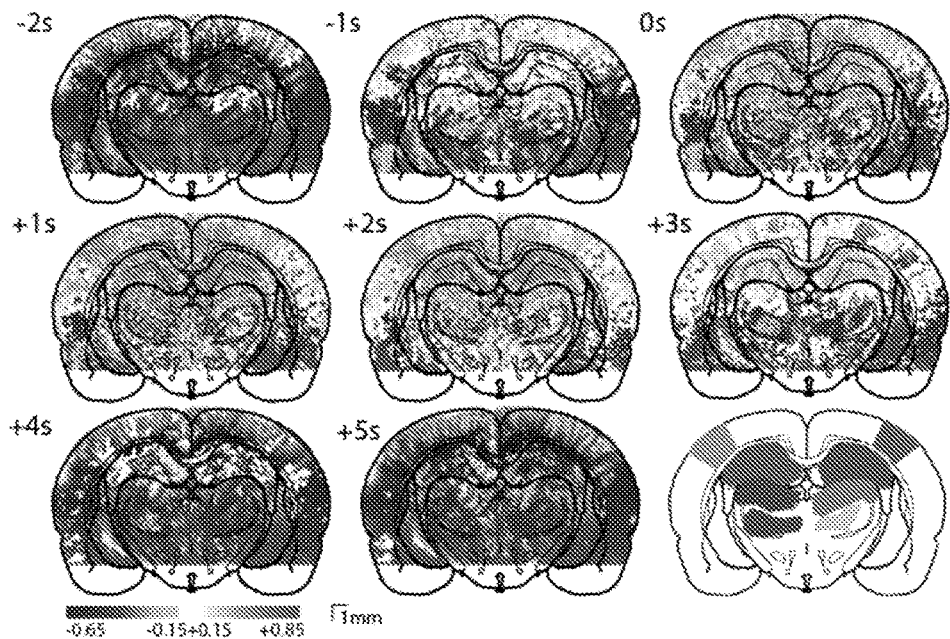
Figure 15:
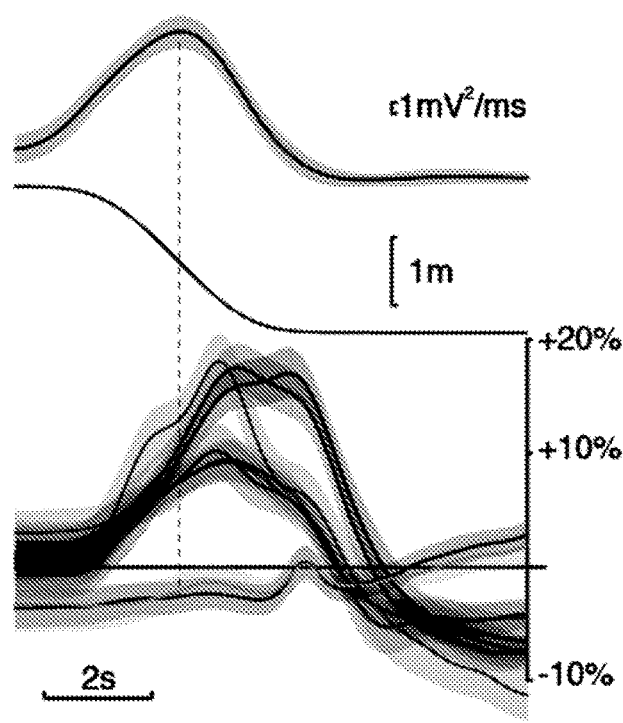
Figure 16:
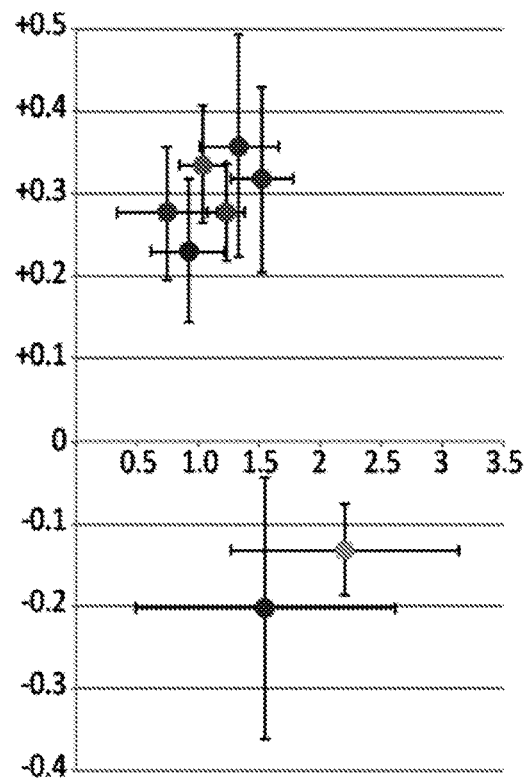

For FIGS. 14 to 16, maze experiment cross-correlation (see FIG. 14) between LFP theta band power and ultrasound signal for each pixel at varying time lag (−2 to +5 s) over n=20 midline crossings acquired in one hour. Widespread hyper-perfusion occurred between −1 and +3 s, together with hypo-perfusion in ventral thalamus. Region variation of hemodynamic signal is obtained by spatial averaging of pixels indicated on atlas layout (mean+/−sd envelop). Mean theta power (purple) and trajectory (green). The vertical dotted line shows the reference midline-crossing time (see FIG. 15). Value and delay of peak Pearson's R (see FIG. 16) shows close responses between left and right dorsal thalamus, hippocampus, and primary sensory cortex.

Figure 17:
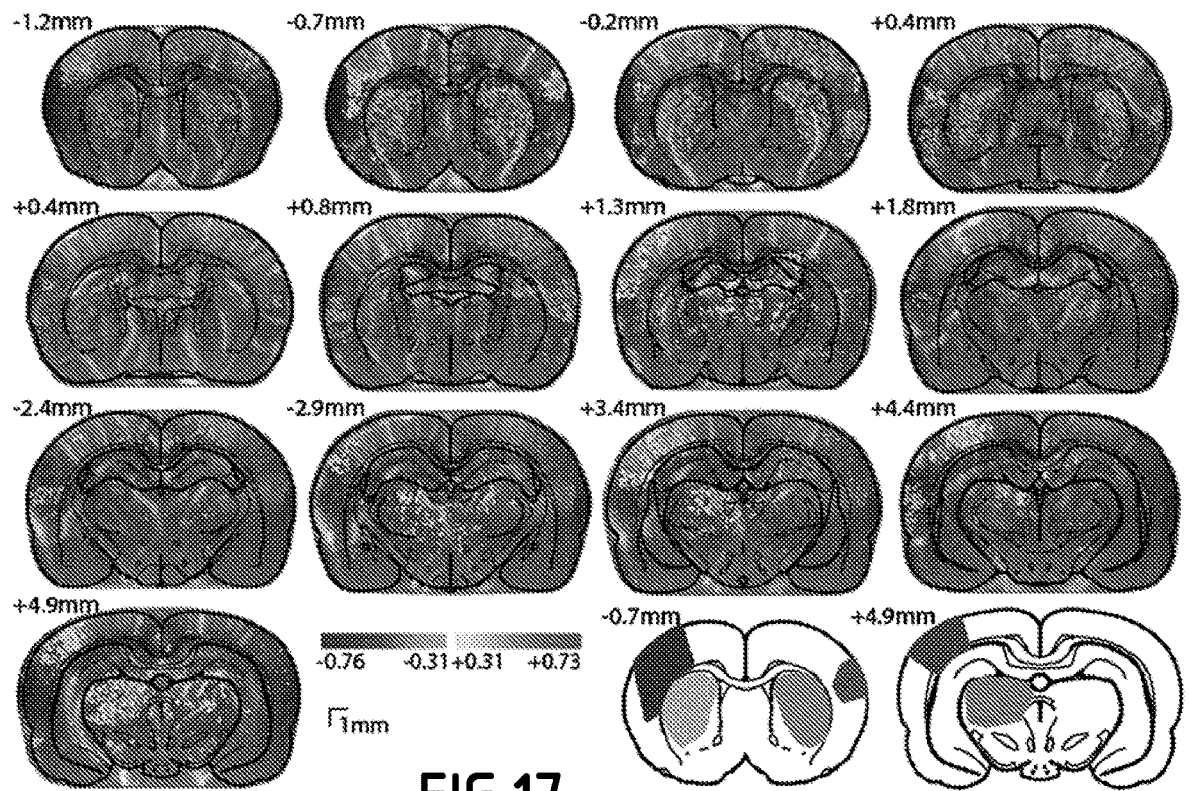

For FIGS. 17 to 20, epilepsy experiment cross-correlogram between mfUS image and seizure, at zero time lag, for successive coronal planes (see FIG. 17). The sensory cortex showed several hyper-perfusion patches on one hemisphere and none on the other. Caudal thalamus was also significantly hyper-perfused. Hypo-perfusion was found in the CPu and some cortical areas. Averaging areas color-marked on atlas layouts showed bilateral fluctuations in the CPu (see FIG. 18). On the contrary, the cortex showed transient bilateral or unilateral co-activation, even though seizures were always bilateral on the EEG. Synchronous oscillations in the seizing cortex and thalamus were found in caudal planes (see FIG. 19). Average over significant areas consistently showed hyperperfusion in sensory cortex and thalamus versus hypoperfusion in CPu, and stable hippocampus perfusion (see FIG. 20).

For FIGS. 14 and 17, significant pixels are shown for $p<10^{-2}$ with Bonferroni correction.

FIGS. 21 to 24 illustrate the effect of recording procedure on running and seizure.

Figure 21:
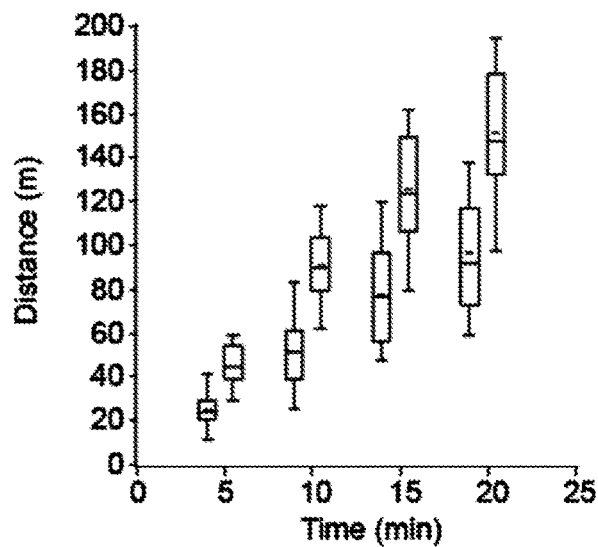
Figure 22:
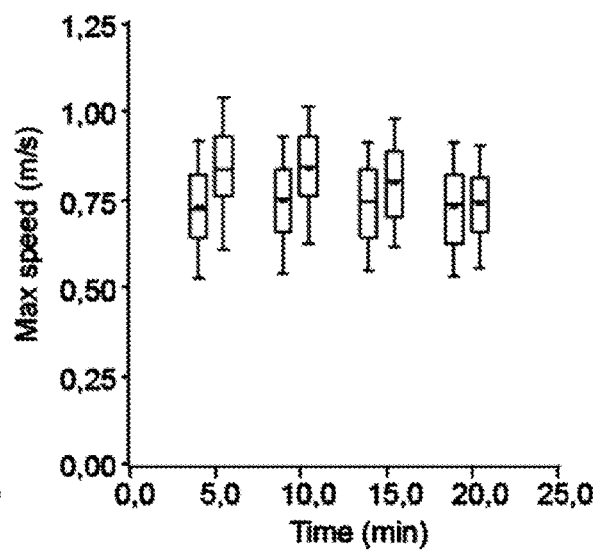

On FIGS. 21 and 22, maze experiment comparative distributions between mfUS-EEG (blue) and control untethered, surgery free, rats (red) show cumulative distance travelled in the maze is reduced by 36-44% while maximum speed is moderately reduced by 1-13%.

Figure 23:
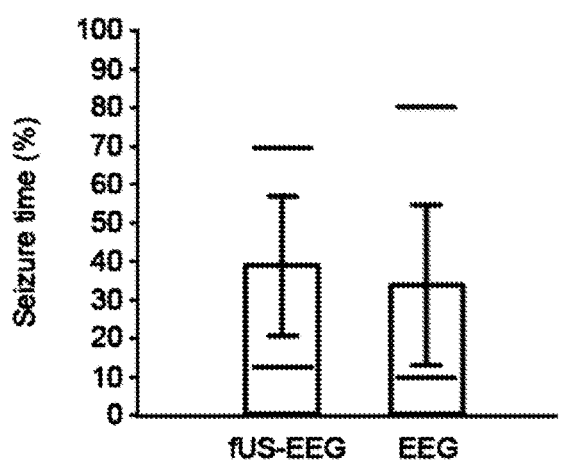
Figure 24:
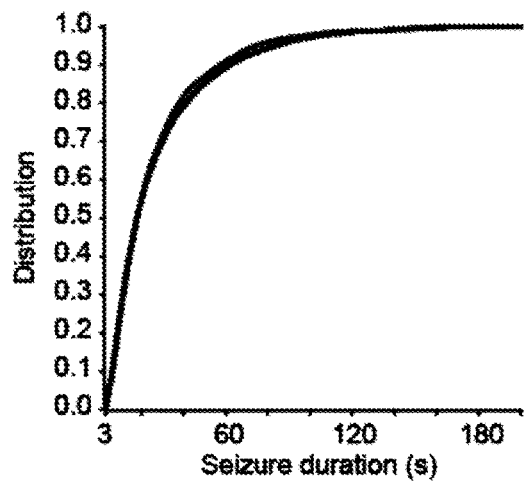

On FIGS. 23 and 24, genetic absence rats (GAERS, blue) show equivalent seizing time fraction and seizure duration distribution compared to EEG-only recordings (red).

FIGS. 25 to 27 are Photographs of the miniature ultrasound probe (see FIG. 25), micromotor (see FIG. 26). The probe holder (see FIG. 27) is composed of a plate fixed onto the head (right) and a translation stage (left).

Tables

The experiments carried out are also illustrated by the following tables.

TABLE 1

Maze travelled distance (m)

|  | 5 minutes | 10 minutes | 15 minutes | 20 minutes |
| --- | --- | --- | --- | --- |
| mfUS-EEG | 25.1 +/− 8.4 n = 19 | 51.2 +/− 17.1 n = 19 | 77.2 +/− 23.4 n = 18 | 96.0 +/− 26.8 n = 18 |
| Untethered | 44.7 +/− 9.2 n = 21 | 90.8 +/− 17.3 n = 21 | 125.1 +/− 26.1 n = 21 | 151.3 +/− 31.5 n = 21 |
| p (Student) | 2E-8 | 1E-8 | 7E-7 | 1E-6 |
| ratio | 56% | 56% | 62% | 64% |

Cumulative distance travelled over time, from the beginning of the task, for EEG-mfUS and surgery-free, untethered, control rats. The two groups performed significantly differently, with a ratio of performance around 60%.

TABLE 2

Maze maximum speed (m/s)

|  | 0-5 minutes | 5-10 minutes | 10-15 minutes | 15-20 minutes |
| --- | --- | --- | --- | --- |
| mfUS-EEG | 0.728 +/− 0.120 n = 191 | 0.739 +/− 0.131 n = 202 | 0.737 +/− 0.119 n = 181 | 0.726 +/− 0.124 n = 135 |
| Untethered | 0.835 +/− 0.132 n = 430 | 0.834 +/− 0.122 n = 448 | 0.789 +/− 0.121 n = 326 | 0.732 +/− 0.106 n = 245 |
| p (Student) | <1E-8 | <1E-8 | 3E-6 | 0.59 (NS) |
| ratio | 87% | 89% | 93% | 99% |

Maximum speed during maze end-to-end walk for successive 5 min time windows, for EEG-mfUS and surgery-free, untethered, control rats. The two groups performed slightly, yet significantly, differently for the first 15 min, with a ratio of performance in the range of 87%-93. After 15 min the difference between the two groups fell to 1%, which is not significant.

TABLE 3

Absence seizure pattern

|  | Recording seizure fraction (%) | Seizure duration (s) |
| --- | --- | --- |
| mfUS-EEG | 38.8 +/− 18.2 n = 65 | 5 +/− 30.2 n = 6372 |
| EEG | 33.7 +/− 20.1 n = 18 | 26.4 +/− 34.3 n = 875 |
| p | 0.31, NS (Student) | 0.98, NS (Kolmogorov) |

Comparison of EEG seizure patterns in epileptic rats, between craniotomized EEG-mfUS rats and controls without cranial window. The recording seizure fraction counts the proportion of time exhibiting seizure over the whole recording session. Duration of all detected seizures is also compared. Both indicators of seizure pattern showed non significant differences between the two groups, supporting a minimal effect of the experimental procedure on seizure activity.

General Presentation of the Set-Up of the Experiences

We present the details of this general methodological frame below (see FIGS. 4 to 13) and then we demonstrate two tailored applications (see FIGS. 14 to 20), first to search for the functional correlate of theta rhythm, known to be involved in brain area communication in spatial navigation tasks, and, second, to explore the neuronal and metabolic manifestations of spontaneous generalized epileptic seizures, as how absence seizures initiate and generalize remain a debated question with a clinical impact.

In this experimental study, we separate the surgical procedure to prepare the animal for imaging from the later chronic recording sessions (see FIGS. 4 to 8). Craniotomy of the parietal and frontal skull bones (15 mm AP×14 mm ML) exposes the dura mater. Intracranial stereotaxic electrodes are implanted, anchored on the edges of the window and their connector is fixed to the back of the head. Finally, a polymer prosthesis is sealed in place of the skull. High contrast is obtained with a polymethylpentene film of 125 µm thickness, offering excellent ultrasound clarity, mechanical resistance and low permeability to water and gas. Thus we achieve observational access to the cortex and deep structures, with larger and deeper field of view, and improved sensitivity over earlier cranial thinning procedures.

Three nuts used as attachment points for the probe holder are sealed above the nasal and lateral to the intraparietal bones, and the animal is allowed a recovery period. Ultrasound recordings use a miniature ultrasound probe (18 mm radius, 25 mm height) mounted on a lightweight head-anchored adjustable holder (18 g, see FIGS. 25 to 27). The device is fixed to the head under light isoflurane anesthesia, with contact gel between the probe and prosthetic skull. The holder is motorized to explore consecutive planes, without direct interaction between the experimenter and the animal, and can be locked for maximum stability.

Animal Preparation

All animals received humane care in compliance with the European Communities Council Directive of 2010 (2010/63/EU), and the study was approved by the institutional and regional committees for animal care. Adult Sprague Dawley rats aged 10-12 weeks and GAERS (Genetic Absence Epilepsy Rat from Strasbourg) aged 8-16 weeks underwent surgical craniotomy and implant of ultrasound-clear prosthesis. Anesthesia was induced with 2% isoflurane and maintained by ketamine/xylazine (80/10 mg/kg), while body temperature was maintained at 36.5° C. with a heating blanket (Bioseb, France). A sagittal skin incision was performed across the posterior part of the head to expose the skull. Parietal and frontal flaps were excised by drilling and gently moving the bone away from the dura mater. The opening exposed the brain between the olfactory bulb and the cerebellum, from Bregma +6 to Bregma −8 mm, with a maximal width of 14 mm. A plastic sheet of polymethylpentene was sealed in place with acrylic resin (GC Unifast TRAD) and residual space was filled with saline. We chose a prosthesis approach which offers larger field of view and prolonged imaging condition over 1-2 month, compared to the thinned bone approach. Particular care was taken not to tear the dura in order to prevent cerebral damage. The surgical procedure, including electrode implantation, typically took 4-6 h. Animals recovered quickly, and after a conservative one week resting period they were used for data acquisition. In order to attach the probe before a recording session, rats were lightly anesthetized for 20-25 min with 2% isoflurane and left to recover for 30 min after waking up.

Electrodes

Intra-hippocampal handmade theta electrode bundles are composed of 25 µm insulated tungsten wire, soldered to miniature connectors. Four to six conductive ends are spaced by 1 mm and glued to form 3 mm-long, 50 µm thick bundles. The bundles are lowered in dorsal hippocampi at stereotaxic coordinates AP=−4, ML=+/−2.5, DV=−1.5 to −4.5, in mm relative to Bregma. Hippocampal theta rhythm is confirmed by phase inversion across recording sites in successive hippocampal layers, time-frequency decomposition, and coincidence with periods of exploration and navigation. Two epidural screws placed above the cerebellum are used as reference and ground. Absence epilepsy recording used four bipolar electrodes implanted in primary somatosensory cortex: S1BF=AP−3, L+/−5, DV−1.75 and S1Lp=AP+1, L+/−6, DV−2, in mm relative to Bregma.

Animal Behavior

Animals for the maze experiment were trained before surgery. They were placed under a controlled water restriction protocol (weight between 85 and 90% of the normal weight) and trained to run back and forth in a long rectangular maze for water reinforcement. The maze (225×20 cm) had 5 cm high lateral walls, and was placed 50 cm above ground. Drops of water were delivered through two small tubes coming out from the two end walls of the maze (see FIGS. 9 to 11). Each time the animal crossed the maze, a single drop of water was delivered in alternate water tubes by opening an electronically controlled pair of solenoid valves. Daily training lasted 30 min. Rats took about 2 sessions to reach a 60 crossing criterion and perform reliably, crossing the maze at fast speed, but were reinforced for at least two more days. Daily recording sessions lasted 20 to 30 min, depending on animal motivation. Since the acquisition in "burst mode" required 40 s for image reconstruction from ultrasound echoes, we could not capture every run. The number of runs acquired ranged from one fourth to one half of all the runs, depending on animal performance and the timing of its spontaneous runs within the session. The data analyzed here were recorded in 12 sessions performed across 8 days. Epileptic animals were recorded in a regular housing cage with cover removed.

Miniature Ultrasound Probe

The ultrasonic probe is a linear array made of 128 transducers (spatial pitch 0.11 mm) working at a 15 MHz central frequency, enabling a typical 100×100 µm resolution in the imaging plane (Vermon, Tours, France). This probe has an acoustic lens with an elevation focal distance of 8 mm and an elevation focal width of 400 µm. The active part is embedded in 18.5 mm diameter and 25 mm length molded resin. A 150 cm cable length and 12 g probe weight ensure a good freedom and comfort to move for the animal.

Probe Holder

The holder is made of two parts machined in Plexiglas for light weight and stiffness. First, a base plate with U-shaped side grooves, allowing translation of the mobile part, is attached to the head of the animal with three screws. Second, the mobile part presenting two sliding side edges is fitted into the base part. The probe is attached through a central opening in the mobile part. A linear servo motor (Robotshop.com, VS-19) is fixed to the mobile part and anchored on the base plate. It is controlled by custom made electronics connected to the ultrasound scanner through USB port. Holder weight is 18 g, and overall size 41 mm width, 34 mm length, 16 mm height.

Ultrasound Acquisition

Vascular images are obtained via the Ultrafast Compound Doppler Imaging technique. The probe is driven by a fully programmable GPU-based ultrafast ultrasound scanner (Supersonic Imagine, Aix-en-Provence, France) relying on 24 Gb RAM memory. In "burst mode" we used an acquisition sequence of 6000 frames at a rate of 500 Hz for a total acquisition time of 12 s. Manual trigger was given when the animal finished drinking water, and turned around in position for the next run. In the "continuous mode", we acquired 200 ultrasound images at 1 kHz frame rate for 200 ms, repeating every 3 s. In both "burst mode" and"continuous mode" each frame is a Compound Plane Wave frame, that is, a coherent summation of beamformed complex in phase/quadrature images obtained from the insonification of the medium with a set of successive plane waves with specific tilting angles. This compound plane wave imaging technique enables to recreate a posteriori a good quality of focalization in the whole field of view with very few ultrasound emissions. Given the tradeoff between frame rate, resolution and imaging speed, a Plane Wave Compounding using five 5°-apart angles of insonification (from −10° to +10°) has been chosen. As a result, the pulse repetition frequency (PRF) of plane wave transmissions was equal to 8 kHz. In order to discriminate blood signals from tissue clutter, the Ultrafast Compound Doppler frame stack is high pass filtered using a 4th order Butterworth filter (cut-off frequency 50 Hz) along the temporal dimension, giving a high frequency in phase/quadrature frame stack whose energy in each pixel is then computed to build the ultrafast Power Doppler fUltrasound image. Some frames are discarded before being incorporated in a recording when they show artifact echoes, which are caused by the animal bumping the probe against a hard surface such as cage or maze wall.

EEG Acquisition

Intracranial electrode signals are fed through a high input impedance, DC-cut at 1 Hz, gain of 1000, 16 channel amplifier and digitized at 20 kHz (Xcell, Dipsi, Cancale, France), together with a synchronization signal from the ultrasound scanner. Custom made software based on Labview (National Instruments, Austin, Tex., USA) simultaneously acquires video from a camera pointed at the recording stage.

Analysis

Data is collected from ultrasound and video-EEG for offline processing, with custom made software. Playback and analysis software is implemented with Labview. Signals are synchronized across modalities.

Animal position is detected by applying a threshold on the image pixel intensity that distinguish the bright animal on dark background. Cumulative distance and maximum crossing speed are computed using the trajectory smoothed with a time constant of 0.5 s.

Ultrasound images are normalized according to the average value over all the non-running or non-seizing time, thus giving the relative change in vascular echo in percent of baseline. Paxinos atlas is superimposed using the cortex as the main landmark. Statistical significance on images used Bonferroni correction to account for the multiple testing over the large number of pixels.

EEG is filtered pass-band 6-9 Hz for hippocampal theta. Power of theta is computed as the square of the EEG signal integrated over a sliding window of characteristic width 0.5 s. Epileptic seizures are detected when EEG electrodes presents at least 3 s of spikewave at a rate above 5 Hz, while a spikewave interval of 3 s discriminates consecutive seizures.

Computation of Pearson's R correlation coefficient between EEG and mfUS pixel intensity is based on theta power curve for the maze experiment. For the epilepsy experiment pixel intensity is correlated to seizure status function (1 inside seizure, 0 outside). Statistical test is performed on Pearson's R coefficient using Student's t-distribution.

All statistics are given as mean+/−standard deviation.

First Experiment

We first recorded from rats walking along a linear maze, to address how brain-wide networks activate during periods of hippocampal theta rhythm, which is a major mechanism proposed for intracerebral cross-area processing in episodic memory and spatial navigation tasks. Healthy Sprague Dawley rats (n=8) ran on a 2.25 m long, 0.2 m wide linear track for water reward. A single imaging plane included dorsal hippocampus, cortex with somatosensory areas, and thalamus. In order to temporally resolve hemodynamics as the animal crossed the maze we used a "burst mode" ultrasound sequence (see FIGS. 9 to 11), acquiring fUS compound frames at 500 Hz for 12 s. Acquisition was triggered when the animal turned around, and was followed by a 40 s lapse to collect the data. As expected, hippocampal theta was consistently associated with locomotion. Distance travelled over time was slower (56% to 64%) than in control untethered, surgery-free, rats ($p<10^{-6}$, see FIGS. 21 to 24, tables 1 and 2). Yet, maximum speed was only slightly slower for the initial 15 min, with the difference reducing to non significant 1% thereafter. In order to analyze series of track crossing trials, we aligned them by setting each trial reference time when the rat crossed the middle of the maze.

In this experiment single pixel variations ranged from −30% to +60% (see FIGS. 9 to 11), while brain area averages reached −10 to +20% (see FIG. 15). As expected, theta band intra-hippocampal EEG power peaked at top animal speed, which was coincident with crossing the midline, with a mid-height theta peak width of 3.2+/−0.3 s (n=8). In order to quantify functional activation during the task, we computed the maps of Pearson's correlation coefficient between power in the theta band and pixel intensity, for varying time lags (see FIG. 14). Averaging pixels across anatomical areas revealed hyper-perfusion in the somatosensory cortex, dorsal thalamus and hippocampus, and hypoperfusion in the ventral thalamus. These correlations were consistent with fUltrasound signal time course (see FIG. 15). Hyperemia peaked at 0.7-1.5 s following the peak of hippocampal theta, which is compatible with signaling cascades that adapt blood flow to cognitive demand implied by the task. The occasional asymmetry that we observed between left and right cortical hemispheres may correlate with functional dominance. Overall (see FIG. 16), our data reveal a pattern of combined hippocampal and widespread cortical activation in a short time window around the navigation task, with coordinated thalamic suppression. This pattern is coherent with observations in still animals, in the context of spontaneous activity during a conditioning protocol, which described thalamic suppression during hippocampo-cortical interaction involved in episodic memory operations. In the present locomotion task, the dorsal thalamus is activated simultaneously with a suppression in the ventral thalamus.

Second Experiment

In a second experiment we scanned through the brain of an epileptic rat, to address the heterogeneous alterations in neuro-metabolic coupling during hypersynchronous seizure activity. Spontaneous generalized absence seizures were recorded from bilateral cortical electrodes in Genetic Absence Epilepsy Rats from Strasbourg (GAERS, n=12). We quantified both the relative time spent seizing and seizure duration, and found no significant difference between EEG only and EEG-mfUS conditions (see FIGS. 16 and 17 and table 3). A "continuous mode" of ultrasound acquisition was used (see FIG. 16), alternating 200 ms to generate one compound mfUS image followed with 2.8 s of processing. Multiple imaging planes were scanned for 10 min to 15 min each.

Figure 18:
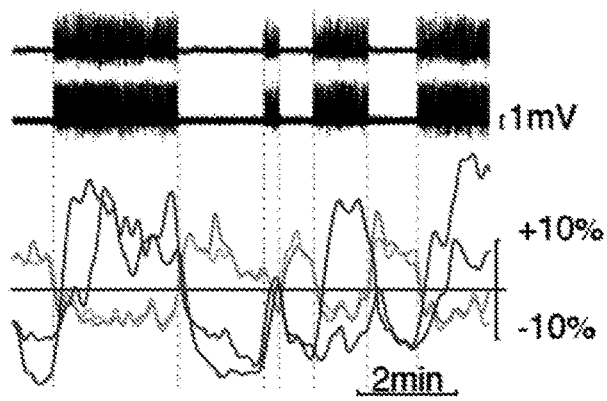
Figure 19:
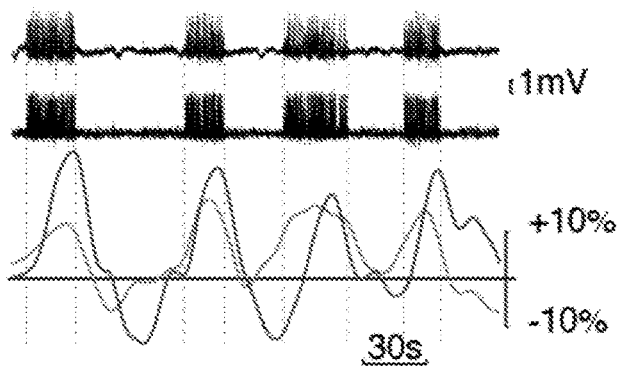
Figure 20:
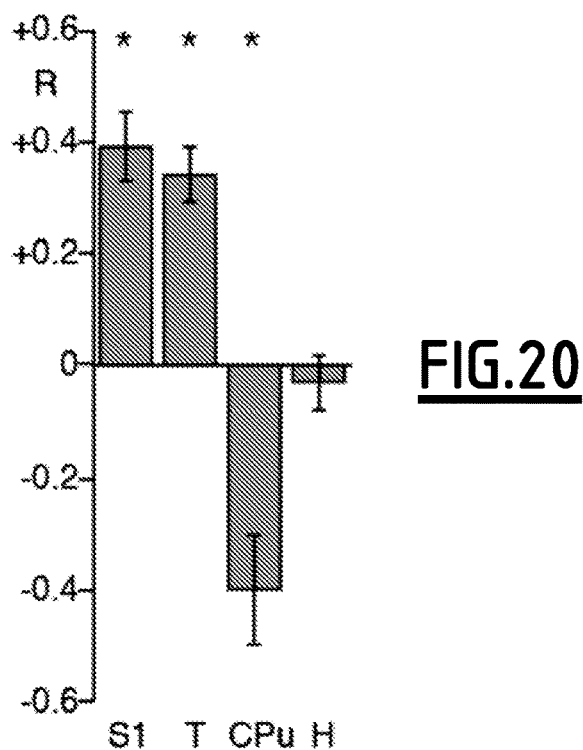

In this experiment, we also found individual pixel changes in the range from −30% to +60% (see FIGS. 12 and 13), while averaging over seizure-associated areas revealed changes from −10% to +20% (see FIGS. 18 and 19). We found distinct patterns of correlation across structures along the antero-posterior axis. Hyper-perfusion in the somatosensory cortex and thalamus was concomitant with hypoperfusion in the Caudate Putamen (CPu) and no variation in the hippocampus. Although absence seizures are generalized throughout neocortex, vascular alterations showed spatial compartments, and lateralization in the frontal primary sensory cortex perfusion was observed in half of the animals [6/12 rats]. Furthermore, the sensitivity of mfUS revealed that consecutive seizures with a similar bilateral cortical EEG profile could display distinct bilateral or unilateral perfusion course (see FIG. 18). Comparing the dynamics of cortical and thalamic areas coupled to seizure (see FIG. 19) revealed synchronous oscillations in the perfusion pattern. Thus, the responses we observed across anatomical structures (see FIG. 20) are compatible with EEG-fMRI experiments that found inversed electrographic-hemodynamic coupling between the cortex and CPu, and with time-resolved EEG-NIRS experiments that indicate blood flow fluctuations around seizures initiation. With the best of time and spatial resolution of these two techniques, mfUS further points to cortical decoupling between electrographic activity and perfusion, with both static and transient components, in naturally occurring seizures.

CONCLUSION

We have developed a new experimental tool that captures the hemodynamic state of the brain over its whole depth along with its electrographic activity in awake, mobile rats over repeated and prolonged periods of time. In two illustrative paradigms we demonstrated how this tool applies to both cognitive and pathological questions.

Thus, significant progress was achieved to observe the interplay between metabolism and neuronal electrical activity that govern global brain equilibrium. While current plane-by-plane imaging imposes to choose appropriately oriented plane to address questions such as hippocampal-prefrontal cortex interaction, synchronous multiple plane acquisition will become possible with future matrix-type probes. As it develops, ultrasound imaging becomes applicable to a wide range of protocols including complex behavioral tasks in healthy subjects and neurovascular pathologies.

To deploy the potentialities of fUltrasound we have developed here the proof of concept for the extension of the technique to awake and mobile rats (mfUS). Furthermore, in such condition we demonstrate the possibility to combine recording of cerebral hemodynamics at high spatiotemporal resolution and sensitivity, with simultaneous monitoring of neuronal activity through EEG. We have developed an integrated experimental setup that relies on a set of technological advances: an ultrasound permeable skull prosthesis, a lightweight ultrasound probe, a motorized head-mounted probe holder, electrode implantation procedure and software environment for synchronized acquisition, playback and analysis of these multimodal signals.

The invention claimed is:

1. Detecting apparatus for imaging at least two areas of a brain of a subject, a first area of the brain being distinct from a second area of the brain, the detecting apparatus being characterized in that the detecting apparatus comprises:
   a holder comprising:
      a frame devoted to be fixed, notably cemented, on a part of the skull of the subject, the frame delimitating an inner portion which is transparent to ultrasound waves,
   a removable imaging device comprising:
      a platform delimitating an inner space the inner space facing the inner portion,
      a fixing element adapted to temporary fix and lock the platform to the holder,
      an ultrasound probe comprising one or more transducer arrays, and
      a moving stage holding the ultrasound probe, and being adapted to move the ultrasound probe within the inner space, the moving stage being adapted to move between a first position wherein the first area of the brain is imaged with the ultrasound probe and a second position wherein the second area of the brain is imaged with the ultrasound probe.

2. Detecting apparatus according to claim 1, wherein the holder further comprises a window transparent to ultrasound waves, the window being inserted in the frame such that the window corresponds to the inner portion.

3. Detecting apparatus according to claim 1, wherein the fixing element and the frame are magnetic.

4. Detecting apparatus according to claim 1, wherein the frame further comprises an element having a first shape, the fixing element having a second shape, the first shape and the second shape being complementary.

5. Detecting apparatus according to claim 1, wherein each transducer array is a linear transducer array.

6. Detecting apparatus according to claim 1, wherein the moving stage comprises a movable screw.

7. Detecting apparatus according to claim 6, wherein the moving stage further comprises a motor adapted to move the screw and a controller adapted to command the motor with a command law.

8. Detecting apparatus according to claim 7, wherein the command law depends on at least one of the following elements:
   the amplitude of reflected ultrasound signal obtained by the ultrasound probe over an object with a known position such as a wire or bead,
   images obtained by the ultrasound probe using a Doppler technique,
   images obtained by the ultrasound probe using an ultra-sensitive Doppler technique, and
   a reference structural atlas.

9. Detecting apparatus according to claim 7, wherein the removable imaging device further comprises at least one additional sensor adapted to provide a continuous signal, each additional sensor being chosen among an electrode, an implanted electrode, an accelerometer, a camera adapted to film the subject and wherein the command law depends from the signal from the additional sensor.

10. Detecting apparatus according to claim 7, wherein the removable imaging device further comprises a unique cable, the cable being positioned between the platform and the controller.

11. Detecting apparatus according to claim 1, wherein the moving stage is a translating stage adapted to translate the ultrasound probe within the inner space.

12. Detecting apparatus according to claim 1, wherein the moving stage is a rotating stage adapted to rotate the ultrasound probe around an axis within the inner space.

13. Method for imaging at least two areas of a brain of a subject, a first area of the brain being distinct from a second area of the brain, the method comprising the steps of:
   providing a holder comprising:
      a frame devoted to be fixed, notably cemented, on a part of the skull of the subject, the frame delimitating an inner portion which is transparent to ultrasound waves,
   fixing, notably cementing, the frame to the part of the skull of the subject,
   providing a removable imaging device comprising:
      a platform delimitating an inner space, the inner space facing the inner portion,
      a fixing element adapted to temporary fix and lock the platform to the holder,
      an ultrasound probe comprising one or more transducer arrays, and
      a moving stage holding the ultrasound probe and being adapted to move the ultrasound probe within the inner space,
   fixing the platform to the holder with the fixing element,
   imaging a first area of the brain with the ultrasound probe,
   moving the ultrasound probe with the moving stage, and
   imaging a second area of the brain with the ultrasound probe.

14. Method for imaging according to claim 13, wherein the subject is awake.

* * * * *